United States Patent [19]
Haas et al.

[11] Patent Number: 6,013,812
[45] Date of Patent: Jan. 11, 2000

[54] PROCESS FOR THE PRODUCTION OF FIVE-MEMBERED OR SIX-MEMBERED CYCLIC ETHERS, IN PARTICULAR OF ANHYDROPOLYOLS

[75] Inventors: Thomas Haas, Frankfurt; Olaf Burkhardt, Alzenau; Marcus Morawietz, Hanau; Rudolf Vanheertum, Kahl, all of Germany; Agnes Bourrel, Lyons, France

[73] Assignee: Degussa Aktiengesellschaft, Frankfurt, Germany

[21] Appl. No.: 09/182,510

[22] Filed: Oct. 30, 1998

[30] Foreign Application Priority Data

Nov. 7, 1997 [DE] Germany .......................... 197 49 202

[51] Int. Cl.⁷ ...................... C07D 307/06; C07D 309/04
[52] U.S. Cl. .......................................... 549/416; 549/475
[58] Field of Search ...................... 549/416, 475

[56] References Cited

FOREIGN PATENT DOCUMENTS

89/00162   1/1989   WIPO .

OTHER PUBLICATIONS

Bock et al., Acta Chemica Scandinavica, B35 (1981) pp. 441–449.

Primary Examiner—Johann Richter
Assistant Examiner—Taofiq A. Solola
Attorney, Agent, or Firm—Smith, Gambrell & Russell, LLP; Beveridge, DeGrandi, Weilacher & Young

[57] ABSTRACT

The present invention relates to a process for the production of five-membered or six-membered cyclic ethers, in particular of anhydropolyols, by acid-catalysed cyclodehydration of polyols that contain at least two hydroxyl groups with a spacing enabling ring formation—that is to say, preferably with a spacing of 4 or 5 C atoms. The invention is directed in particular towards the production of anhydrotetritols, anhydropentitols and, particularly preferred, anhydrohexitols, from tetritols, pentitols and hexitols, respectively.

22 Claims, No Drawings

PROCESS FOR THE PRODUCTION OF FIVE-MEMBERED OR SIX-MEMBERED CYCLIC ETHERS, IN PARTICULAR OF ANHYDROPOLYOLS

INTRODUCTION AND BACKGROUND

The present invention relates to a process for the production of five-membered or six-membered cyclic ethers, in particular of anhydropolyols, by acid-catalysed cyclodehydration of polyols that contain at least two hydroxyl groups with a spacing enabling ring formation—that is to say, preferably with a spacing of 4 or 5 C atoms. The invention is directed in particular towards the production of anhydrotetritols, anhydropentitols and, particularly preferred, anhydrohexitols, from tetritols, pentitols and hexitols, respectively.

The acid-catalysed cyclodehydration of polyhydric alcohols accompanied by the formation of, in particular, 5-membered cyclic ethers or hydroxyethers, designated hereinafter as anhydropolyols, has been known for a long time. The cyclodehydration of a sugar alcohol from the family of the hexitols results in a complex product mixture of anhydrohexitols and dianhydrohexitols as well as undesirable by-products arising by virtue of the production process, among them polymers; see K. Bock et al. in *Acta Chemica Scandinavica* B 35 (1981) 441–449 and G. Flèche et al. in *Starch/Stärke* 38 (1986) No. 1, 26–30. Increasing interest is being shown in anhydropolyols that can be produced from renewable raw materials such as sugars, for instance 2,5-sorbitan and isosorbide from D-glucose or sucrose via sorbitol, in connection with the production of polyester resins, epoxy resins and surfactants.

In the article by G. Flèche cited above, the influence of the water content, the type of acid and the acid concentration on the composition of the product and the polymer content in connection with the acid-catalyzed cyclodehydration of sorbitol obtained by hydrolysis of starch and hydrogenation of the D-glucose arising in the process is dealt with. This article recommends that dehydration be carried out, as far as possible, in the absence of water. Mineral acids, organic cation-exchangers or Lewis acids are employed as catalysts. The use of mineral acids or Lewis acid as catalysts necessitates neutralization and elaborate separation of the salt from the reaction mixture and disposal of the salt. A disadvantage of all forms of implementation is the usually high polymer content in the reaction mixture. The polymer content is particularly disadvantageous when the reaction mixture is to be supplied directly—that is to say, without further elaborate purifying stages—to a stage for further utilization after removal by distillation of the isosorbide which is formed.

According to DE-OS 31 11 092 cyclodehydration can also be carried out by means of gaseous hydrogen halide such as HCl as catalyst and, optionally in addition, of an organic carboxylic acid as co-catalyst. Disadvantages of this process include the very large quantity of catalyst required, as well as the small proportion of monoanydro products produced. According to WO 89/00162 the cyclodehydration of hexitols can also be carried out at moderate temperature in liquid hydrogen fluoride in the presence of a carboxylic acid, but this process is very elaborate on account of the great dangers of HF to both people and material.

Instead of using acidic catalysts, the cyclodehydration of polyols such as glucitol can also be catalyzed by means of bimetallic catalysts such as Cu—Pt, Cu—Au, Cu—Pd and Cu—Ru in the presence of hydrogen; see C. Montassier et al., *Applied Catalysis A: General* 121 (1995), 231–244. However, in the course of this conversion, with increasing conversion of glucitol (=sorbitol) into monoanhydroglucitols and 1,4:3,6-dianhydroglucitol a decline in dehydration selectivity occurs. Although the selectivity can be increased again by addition of NaCl, the activity of the catalyst falls off considerably in the process.

According to EP-B 0 380 402 it is possible for a maximum of 71% anhydro compounds (49% isosorbide and 22% isomeric monoanhydroglucitols) to be obtained from glucitol. Disadvantages include the high loss (29%) of parent compound, the long reaction times required, and the high catalyst demand or, as the case may be, the necessity for catalyst regeneration. Unless long reaction-times are taken into consideration, the conversion of sorbitol is incomplete, so that the cyclodehydration reaction mixture also contains, besides the monoanhydrohexitols and isosorbide, considerable amounts of sorbitol. Although isosorbide can easily be separated from the mixture by distillation, besides the monoanhydrohexitols the distillation sump remaining contains sorbitol, this latter having a detrimental influence on consequent conversions or necessitating elaborate purification.

Therefore, an object of the present invention is to carry out a process for the cyclodehydration of polyols, in particular of sugar alcohols, that results in substantially quantitative conversion and that leads to cyclodehydration products containing less than 1 wt % polymers.

SUMMARY OF THE INVENTION

The above and other objects of the invention can be achieved by a process for the production of five-membered or six-membered cyclic ethers, in particular of anhydropolyols, by cyclodehydration of polyols having at least 4 C atoms and at least 2 hydroxyl groups, wherein the polyol is treated in the presence of water and an acidic catalyst at a temperature of at least 100° C., said process being characterised in that the treatment is carried out in the presence of an acid-stable hydrogenating catalyst in a hydrogen atmosphere.

In the process according to the invention, polyols are employed that contain at least two hydroxyl groups with a spacing enabling cyclodehydration. Ordinarily the hydroxyl groups are separated from one another by four or five, but preferably four, C atoms, so that in the course of cyclodehydration a 5-membered or 6-membered cyclic ether is formed. It cannot be ruled out that 4-membered cyclic ethers may also be formed in accordance with the invention. The polyols employed preferably contain more than two hydroxyl groups from which anhydropolyols can be formed. The term 'anhydropolyols' in this connection is taken to mean compounds that comprise one, two or more cyclic ethers having five or six members, in particular five members (=dihydrofuran derivatives and, in particular, tetrahydrofuran derivatives), and in addition one or more, in particular two to four, hydroxyl groups. The polyols to be dehydrated contain at least 4 C atoms, ordinarily 4 to 20 C atoms, but polyols having more than 20 C atoms can also be employed, provided that they are sufficiently water-soluble. Polyols having 4 to 6 C atoms and 2 to 6 hydroxyl groups are particularly preferred. The last group includes sugar alcohols from the family of the tetritols such as erythritol, pentitols such as ribitol, arabinitol and xylitol, and hexitols such as glucitol, mannitol, galactitol and iditol. The tetritols, pentitols and hexitols can be employed in the D form or L form, in which they are ordinarily available in naturally occurring raw materials or from such raw materials as can be obtained, or in the form of the racemates or mixtures of conformational isomers.

The cyclodehydration according to the invention is effected in the presence of water. The polyols are ordinarily converted in the form of an aqueous solution, preferably a solution having a polyol content in the range from 10 to 80 wt %, in particular 40 to 60 wt %. Solution may be used, for example, which can be obtained in the course of the transformation of starch into alditols (=hexitols) by hydrolysis with subsequent hydrogenation.

The conversion is effected at a temperature of at least 100° C., mostly in the range from 120 to 380° C. A temperature in the range from 120 to 300° C. is preferred, in particular 180 to 300° C.

As in the state of the art, acidic catalysts are also present in the process according to the invention. Various acids may be used such as the mineral acids $H_2SO_4$, HCl and $H_3PO_4$, organic carboxylic acids and sulfonic acids and also acidic fixed catalysts, the $H_o$ value of the Hammett acidity function of which is less than +2, in particular less than −3. Mineral acids are less preferred, because after the conversion they have to be neutralised and the salts have to be separated from the reaction mixture and disposed of.

In order to make processing of the cyclodehydration reaction mixture as simple as possible, according to a preferred embodiment a carboxylic acid, the boiling-point of which lies below that of the monoandropolyols or dianhydropolyols to be distilled off, in particular a $C_1$ to $C_{12}$ monocarboxylic acid, is employed as catalyst. Particularly preferred is a carboxylic acid from the family comprising formic acid, acetic acid and propionic acid. Such carboxylic acids can be separated by distillation from the reaction mixture and recycled.

The acidic fixed catalysts having $H_o$ less than +2 are substances from the following series: natural and synthetic siliceous substances such as montmorillonite, mordenite and acidic zeolites; acids permanently bonded to inorganic carrier substances such as $SiO_2$, $Al_2O_3$ or $TiO_2$, such as, in particular, phosphoric oxides/acids; oxides such as gamma-$Al_2O_3$, $TiO_2$, $ZrO_2$, $SnO_2$, $Bi_2O_5$, $Sb_2O_5MoO_3$, $WO_3$; mixed oxides such as $SiO_2$—$Al_2O_3$, $SiO_2$—$TiO_2$, $Al_2O_3$—ZnO, $SiO_2$—$ZrO_2$, $SiO_2$—$SnO_2$, $SiO_2$—$MoO_3$, $SiO_2$—$WO_3$; heteropoly acids, for example polytungstosilicates and polytungstophosphates; metallic salts such as $AlPO_4$, $FePO_4$, $Zn_3(PO_4)_2$, $Mg_3(PO_4)_2$, $Ti_3(PO_4)_4$, $Zr_3(PO_4)_4$; cation-exchangers such as exchangers containing sulfonate groups and based on polystyrene, polymeric perfluorinated resins or, preferably, organopolysiloxanes (Deloxan®, available from Degussa AG). Particularly preferred acidic fixed catalysts for the ester formation and ester cleavage according to the invention are zeolites of the H-Y and H-ZSM 5 types.

The required amount of acidic catalysts that are soluble in the reaction mixture generally lies in the range from 0.1 to 20 wt %, in particular from 0.5 to 10 wt %, in each case relative to the polyol. The required amount of solid acidic catalysts depends both on the activity thereof and on the chosen reaction temperature but generally lies within the range of the soluble catalysts. The optimal amount required can be determined simply by means of orienting experiments.

An essential feature of the invention is that, in addition to the acidic catalyst, a conventional hydrogenating catalyst is present and the cyclodehydration is carried out in a hydrogen atmosphere. The partial pressure of hydrogen is generally in the range from at least 0.1 to 20 MPa, preferably in the range from 1 to 15 MPa, and in particular 3 to 10 MPa.

Although homogeneous and heterogeneous catalysts can be employed as hydrogenating catalysts, heterogeneous catalysts are preferred, because a simple separation of the catalyst from the reaction mixture, by filtration for instance, is then possible. Conventional hydrogenating catalysts contain by way of active component a noble metal from the series Ru, Rh, Pd and Pt or a transition metal from the series Cu, Cr, Co, Ni, Fe, including, in particular, Raney catalysts and chromite catalysts; bimetallic catalysts can also be used, consisting of a transition metal and noble metal. Using a hydrogenating catalyst containing one or more transition metals is only expedient when the catalyst exhibits sufficient acid stability under the reaction conditions.

Preferred hydrogenating catalysts for the process according to the invention are noble-metal catalysts in metallic form, such as so-called ethiops of Ru, Rh and, in particular, Pd and Pt, or in a form bound to a carrier. Suitable carrier materials for Ru, Rh, Pd and Pt are activated carbon, aluminium oxide and other metallic oxides and also silicates.

The amount of noble metal in carrier-bound noble-metal catalysts is usually in the range from 0.0001 to 10 wt %, in the case of Pd and Ru preferably in the range from 0.01 to 0.1 wt %. The required amount of noble-metal catalysts, which depends on the activity of the catalyst, the reaction temperature and the pressure of $H_2$, will be ascertained by a person skilled in the art by means of orienting experiments. In general, the required amount is in the range from 0.01 to 10 wt %, in particular 0.5 to 5 wt %, relative to the polyol. Noble-metal catalysts in the form of an ethiops or in carrier-bound form can be easily recycled, and they have a longer useful life than bimetallic catalysts based on a noble metal and a transition metal, such as were employed in the process known previously for cyclodehydration in the absence of an acidic catalyst.

DETAILED DESCRIPTION OF THE INVENTION

The present invention will now be described in greater detail. The process of the present invention can be operated discontinuously or continuously. In this connection the polyol and water can be mixed upstream of the reactor or can be supplied to the reactor in parallel. When an acid is used that is soluble in the reaction mixture by way of catalyst, this is added to the reaction partner, to the water or to the mixture of the two or is introduced into the reactor separately. A solid hydrogenating catalyst can be employed in the form of a suspended catalyst or in the form of a fixed bed. When a solid acidic catalyst is used the latter may find application, in a manner analogous to the hydrogenating catalyst, in the form of a suspension or in the form of a fixed bed. It is also possible to employ a catalyst containing both acidic and hydrogenation-active functions, for example a zeolite that is partially charged with a noble metal. The optimal reaction-time can easily be ascertained by a person skilled in the art by means of orienting experiments.

The cyclodehydration reaction mixture can be processed in simple manner. This processing may comprise the filtration of a solid acidic catalyst and of a heterogeneous hydrogenating catalyst. When a distillable acidic catalyst and a heterogeneous hydrogenating catalyst are used, the processing comprises the filtration of the hydrogenating catalysts and separation of the acidic catalyst by distillation. The reaction mixture remaining after separation of the catalysts is processed by distillation and/or extraction, preferably by distillation. Where necessary, the processing may also comprise a crystallization step. In the case of cyclodehydration of hexitols, dianhydrohexitols that have been formed are mostly separated by distillation, and a mixture of monoanhydrohexitols remains in the distillation sump.

It is a surprising and therefore significant advantage of the process according to the invention that polymers are practically not formed—the rate of formation is below 1 mole %, relative to converted polyol. Hence the reaction mixture which is free from catalysts and water can be utilized further immediately or after separation of distillable dianhydropolyols by distillation.

Monoanhydropolyols, in particular those consisting of hexitols, are therefore valuable raw materials for various fields of application where hitherto the content of polymers was troublesome. Through the preferred use of a low carboxylic acid and a heterogeneous hydrogenating catalyst it is possible to recycle not only the hydrogenating catalyst but also the carboxylic acid, after separation thereof by distillation. When mineral acids, were to be used, hitherto elaborate measures were necessary to separate the salt arising as a result of neutralization of the acidic catalyst from the anhydropolyol reaction mixture. Finally, by virtue of the combination, according to the invention, of an acid catalyst and a hydrogenating catalyst it is possible to employ noble-metal catalysts of high stability, a factor which has an advantageous effect on recyclability and therefore on the costs of the process.

In the course of the cyclodehydration of hexitols, after removal of dianhydrohexitols by distillation it is possible for anhydrohexitol mixtures to be obtained having typical compositions stated in the Table, the concrete composition depending on the chosen reaction conditions.

TABLE

Anhydropolyol mixtures of hexitols after removal of dianhydrohexitols by distillation

| Polyol (substrate) | D-sorbitol (=D-glucitol) | D-mannitol | Dulcitol (Galactitol) |
|---|---|---|---|
| Composition | (%) | (%) | (%) |
| 2,5-anhydro-D-mannitol | 5–50 | | 1–5 *) |
| 2,5-anhydro-L-iditol | 10–50 | | 1–5 *) |
| 1,4-anhydro-D-sorbitol | 10–70 | | |
| 1,4-anhydro-DL-galactitol | | | 65–95 |
| 1,4-anhydro-D-mannitol | 0–10 | 5–20 | 1–5 *) |
| 2,5-anhydro-D-sorbitol | | 50–90 | |
| 1,5-anhydro-D-mannitol | | 5–20 | |
| other polyols | 1–15 | 1–10 | 1–20 |

*) DL form of the anhydro product

These mixtures of substances can be employed for the production of surfactants and also as a component in polycondensation resins and polyaddition resins. In this connection it is to be noted that an increased proportion of 2,5-anhydrohexitols in relation to 1,4-anhydrohexitols has clear advantages in subsequent processing: under unfavourable processing conditions dianhydro compounds can be formed from the 1,4-anhydrohexitols as a result of a further condensation, whereas in the case of the 2,5-anhydrohexitols this reaction is not possible, so that 4 hydroxy functions remain accessible for subsequent processing.

EXAMPLE 1

Into a 20-1 autoclave there were introduced 8 kg D-sorbitol in the form of a 50 wt % solution in water, 5 wt % propionic acid, relative to sorbitol, and 1 wt % Pd/C catalyst having a Pd content of 3 wt %, relative to sorbitol. The reaction mixture was heated to 270° C. and stirred for 2 h at 60 bar $H_2$ pressure. After cooling, the catalyst was removed by filtration and the water/propionic-acid mixture was removed by distillation. According to analysis by gas chromatography the yield relative to D-sorbitol amounted to 38% isosorbide and 58% anhydrohexitols (=tetrols) and less than 1% polymers. The conversion of D-sorbitol was practically quantitative.

Under high vacuum (<10 Pa) at 130° C. 2.5 kg isosorbide (=1,4:3,6-dianhydro-D-sorbitol) were distilled off. The sump (3.9 kg) left behind contained 20% 2,5-anhydro-D-mannitol, 31% 2,5-anhydro-L-iditol, 34% 1,4-anhydro-D-sorbitol and 6% 1,4-anhydro-D-mannitol, 5% isosorbide and about 3% other monomeric polyols, but practically no polymers (<1%)

The analyses of all the Examples and Comparative Examples were carried out by means of GC analytical methods of the silylated polyols on a capillary column (DB-5) at 280° C. Detection is effected in a flame ionisation detector at 250° C. with helium as carrier gas. After retention-times between 15 and 20 min the products were able to be eluted and identified.

EXAMPLE 2

Example 1 was repeated, with the difference that the cyclodehydration was effected for 8 hours at 240° C. According to GC analysis the conversion was greater than 99%; the yields (relative to sorbitol) amounted to 20% isosorbide, 65% monoanhydrohexitols (=tetrols) and less than 1% polymers.

The reaction mixture that was largely free from isosorbide contained 14% 2,5-anhydro-D-mannitol, 21% 2,5-anhydro-L-iditol, 44% 1,4-anhydro-D-sorbitol, 4% 1,4-anhydro-D-mannitol and about 16% other polyols, but less than 1% polymers.

EXAMPLE 3

D-mannitol was employed instead of sorbitol in accordance with Example 1, as a result of which a stereochemically changed product composition was obtained. By way of principal components there were formed (relative to D-mannitol): 48% 2,5-anhydro-D-sorbitol and 23% isomannide (=1,4:3,6-dianhydro-D-mannitol), 10% 1,4-anhydro-D-mannitol and 10% 1,5-anhydro-D-mannitol. The mixture contained less than 1% D-mannitol and less than 1% polymers.

EXAMPLE 4

D-sorbitol was cyclodehydrated in a manner analogous to Example 1, whereby, however, instead of propionic acid an acidic zeolite (type Y zeolite) was employed in an quantity of 1 wt %, relative to D-sorbitol, the reaction temperature amounted to 270° C. and the reaction-time amounted to 4 hours. The conversion of D-sorbitol was practically quantitative (greater than 99%). The yields (relative to sorbitol) amounted to 46% isosorbide, 45% anhydrohexitols, about 8% other low-molecular polyols and less than 1% polymers.

EXAMPLE 5

D-sorbitol was dehydrated in a manner analogous to Example 1, whereby, however, instead of the hydrogenating catalyst Pd/C an Ru/C catalyst was employed having a content of 5% Ru in a quantity of 0.1 wt %, relative to sorbitol. The conversion amounted to 96%; the yields, relative to sorbitol, amounted to 25% isosorbide, 55% anhydrohexitols, about 19% other low-molecular polyols and less than 1% polymers.

EXAMPLE 6

Cyclodehydration was carried out in a manner analogous to Example 5, but sucrose was employed as substrate instead of D-sorbitol; furthermore, conversion was effected for 8 h at 150° C. and then for 4 h at 270° C. In the course of this conversion the hydrogenation of the sucrose to form D-sorbitol and D-mannitol took place in situ with the cyclodehydration. The conversion of sucrose amounted to 95%. The reaction mixture consisted of 29% isosorbide (=1,4:3,6-dianhydro-D-sorbitol), 7% isomannide (=1,4:3,6-dianhydro-D-mannitol), 12% 2,5-anhydro-D-sorbitol, 13% 2,5-anhydro-D-mannitol, 14% 2,5-anhydro-L-iditol, 7% 1,4-anhydro-D-sorbitol, 5% 1,4-anhydro-D-mannitol and 2% 1,5-anhydro-D-mannitol and 11% other low-molecular polyols. Polymers were practically not formed.

EXAMPLE 7

1,4-butanediol was employed as substrate. Conversion was effected otherwise in a manner analogous to Example 1. The conversion of 1,4-butanediol amounted to 76%, the yield of tetrahydrofuran amounted to 52%.

Comparative Example 1
Without Acidic Catalyst

Example 2 was repeated, with the sole difference that no acidic catalyst was employed. After 8 h at 240° C. the conversion of D-sorbitol amounted to 92%. The yields, relative to D-sorbitol employed, amounted to 70% monoanhydrohexitols, 20% isosorbide, about 9% other low-molecular polyols and less than 1% polymers.

This example shows that in the absence of an acid only an insufficient conversion of D-sorbitol is achieved.

Comparative Example 2
(Without Hydrogenating Catalyst and $H_2$)

Example 2 was repeated, with the sole difference that no hydrogenating catalyst was added. With almost quantitative conversion of sorbitol, 8% of the same was transformed into white-yellow polymer. The yields, relative to D-sorbitol employed, amounted furthermore to 29% isosorbide, 54% anhydrohexitols, 9% other low-molecular polyols.

Comparative Examples (CE) 3 to 6

In the absence of an acidic catalyst, sorbitol in the form of a 20-wt % aqueous solution was treated for 8 h at 240° C. and at a $H_2$ pressure of 13 MPa with the hydrogenating catalysts stated in the Table. The conversion of sorbitol and also the yields relative to converted sorbitol of isosorbide and monoanhydropolyols can be gathered from the Table. Polymers arose in each case in a quantity amounting to less than 1%. By way of principal products, polyols arose in the form of $C_2$ to $C_4$ fragments.

| No. | Catalyst | Sorbitol conversion (%) | Monoanhydro-hexitols (= tetrols) (%) | Isosorbide (%) |
|---|---|---|---|---|
| CE 3 | Raney Cu | 95 | 4 | <1 |
| CE 4 | Co—Cu—Mn | 95 | <1 | <1 |
| CE 5 | Raney Ni | 60 | 10 | 2 |
| CE 6 | Cr—Ni | 90 | <1 | <1 |

These tests show that the catalysts investigated are not really suitable for the cyclodehydration.

Further variations and modifications of the invention will be apparent to those skilled in the art from the foregoing and are intended to be encompassed by the claims appended hereto. German priority application 197 49 202.9 is relied on and incorporated herein by reference.

We claim:

1. A process for the production of a five-membered or six-membered cyclic ether, comprising cyclodehydrating a polyol having at least 4 carbon atoms and at least 2 hydroxyl groups, by reacting said polyol in the presence of water and an acidic catalyst and an acid-stable hydrogenating catalyst at a temperature of at least 100° C., and in a hydrogen atmosphere.

2. The process according to claim 1, wherein the cyclic ether is an anhydropolyol.

3. The process according to claim 1, wherein the temperature is in the range from 120 to 380° C. and the hydrogen pressure is in the range from 1 to 20 MPa.

4. The process according to claim 3, wherein the temperature is in the range from 180 to 280° C. and the hydrogen pressure is in the range from 3 to 10 MPa.

5. The process according to claim 1, wherein the hydrogenating catalyst is a catalyst containing one or more noble metals selected from the group consisting of ruthenium, rhodium, palladium and platinum in elemental form or in the form of a noble-metal compound.

6. The process according to claim 3, wherein the hydrogenating catalyst is a catalyst containing one or more noble metals selected from the group consisting of ruthenium, rhodium, palladium and platinum in elemental form or in the form of a noble-metal compound.

7. The process according to claim 4, wherein the hydrogenating catalyst is a catalyst containing one or more noble metals selected from the group consisting of ruthenium, rhodium, palladium and platinum in elemental form or in the form of a noble-metal compound.

8. The process according to claim 1, wherein the hydrogenating catalyst is employed in an amount from 0.001 to 10 wt % relative to the polyol.

9. The process according to claim 1, wherein the hydrogenating catalyst is employed in an amount from 0.01 to 1 wt %, relative to the polyol.

10. The process according to claim 1, wherein the acidic catalyst is an aliphatic carboxylic acid having 1 to 10 carbon atoms.

11. The process according to claim 1, wherein the acidic catalyst is an aliphatic carboxylic acid having 1 to 10 carbon atoms.

12. The process according to claim 1, wherein the acidic catalyst is employed in an amount from 0.1 to 20 wt % relative to the polyol.

13. The process according to claim 1, wherein the acidic catalyst is employed in an amount from 0.5 to 10 wt %, relative to the polyol.

14. The process according to claim 1, wherein the polyol is a member selected from the group consisting of the tetritols, pentitols and hexitols.

15. The process according to claim 1, wherein the catalyst contains acidic and hydrogenation-active functions and based on a zeolite charged with a noble metal selected from the group consisting of Pd, Pt, Ru and Rh and having an $H_o$ value less than +2.

16. The process according to claim 1, wherein the catalyst contains acidic and hydrogenation-active functions and based on a zeolite charged with a noble metal selected from the group consisting of Pd, Pt, Ru and Rh and having an $H_o$ value less than −3.

17. The process according to claim 1 wherein less than 1% by weight of polymers are produced.

18. The process according to claim 1 wherein said polyol is present as an aqueous solution in an amount of 10 to 80% by weight.

19. Anhydrohexitol mixture, obtained by cyclodehydration of sorbitol in accordance with claim 1 with subsequent separation of isosorbide (1,4:3,6-dianhydrosorbitol) from the reaction mixture, the anhydrohexitol mixture comprising 5 to 50% 2,5-anhydromannitol, 10 to 50% 2,5-anyhdroiditol, 10 to 70% 1,4-anhydrosorbitol, 0 to 10% 1,5-anhydromannitol and 1 to 15% other polyols.

20. Anhydrohexitol mixture, obtained by cyclodehydration of mannitol in accordance with claim 1 with subsequent separation of 1,4:3,6-dianhydrommannitol from the reaction mixture, the anhydrohexital mixture comprising 50 to 90% 2,5-anhydrosorbitol, 5 to 20% 1,4-anhydromannitol, 5 to 20% 1,5-anhydromannitol and 1 to 10% other polyols.

21. Anhydrohexitol mixture, obtained by cyclodehydration of dulcitol in accordance with claim 1 with subsequent separation of dianhydrodulcitol, the anhydrohexital mixture comprising 65 to 95% 1,4-anhydrosorbitol, 1 to 5% 2,5-anhydroiditol and 1 to 20% of additional polyols.

22. The process according to claim 1, wherein the acidic catalyst is a monocarboxylic acid selected from the group consisting of formic acid, acetic acid and propionic acid.

* * * * *